US00PP31699P2

(12) United States Plant Patent
Blazkova

(10) Patent No.: US PP31,699 P2
(45) Date of Patent: Apr. 28, 2020

(54) CHERRY TREE NAMED 'HL 13822'

(50) Latin Name: ***Prunus avium* L.**
Varietal Denomination: HL 13822

(71) Applicant: Research and Breeding Institute of Pomology Holovousy Ltd., Horice (CZ)

(72) Inventor: Jitka Blazkova, Horice (CZ)

(73) Assignee: Research and Breeding Institute of Pomology Holovousy Ltd., Horice (CZ)

( * ) Notice: Subject to any disclaimer, the term of this patent is extended or adjusted under 35 U.S.C. 154(b) by 0 days.

(21) Appl. No.: 16/350,126

(22) Filed: Sep. 29, 2018

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Susan McCormick Ewoldt
(74) *Attorney, Agent, or Firm* — The Webb Law Firm

(57) ABSTRACT

A new and distinct variety of cherry tree that produces large fruit with resistance to skin cracking.

3 Drawing Sheets

Botanical classification: *Prunus avium* L.
Varietal denomination: 'HL 13822'.

BACKGROUND OF THE INVENTION

The present invention comprises a new and distinct variety of sweet cherry tree, botanically known as *Prunus avium* L., and referred to by the varietal name 'HL 13822'. The new variety was discovered in Holovousy, the Czech Republic as the result of planned breeding between cherry tree varieties 'Kordia' (female parent, unpatented) and 'Merton Reward' (male parent, unpatented). The new variety was first asexually reproduced via grafting in Holovousy, the Czech Republic. The new variety is similar to 'Kordia' in fruit skin and flesh color, as well as fruit firmness, but differs from 'Kordia' in harvest time, fruit quality, and fruit pedicel length. The new variety is similar to 'Merton Reward' in fruit shape, but differs from 'Merton Reward' in harvest time, fruit quality, fruit pedicel length and skin color. When compared to unpatented cherry tree variety 'Regina', the new variety is similar in harvest time and fruit skin and flesh color, but exhibits a larger fruit size, slightly more susceptibility to fruit cracking, and slightly less fruit firmness. The following characteristics distinguish the new variety from other varieties known to the breeder:

1. Fruit size;
2. Late flowering time; and
3. Resistance to fruit cracking.

The new variety has been trial and field tested and has been found to retain its distinctive characteristics and remains true to type through successive propagations.

DESCRIPTION OF THE DRAWINGS

The accompanying photographic drawings illustrate the new variety with the color being as nearly true as is possible with color illustrations of this type.

DETAILED BOTANICAL DESCRIPTION

Figure 1:
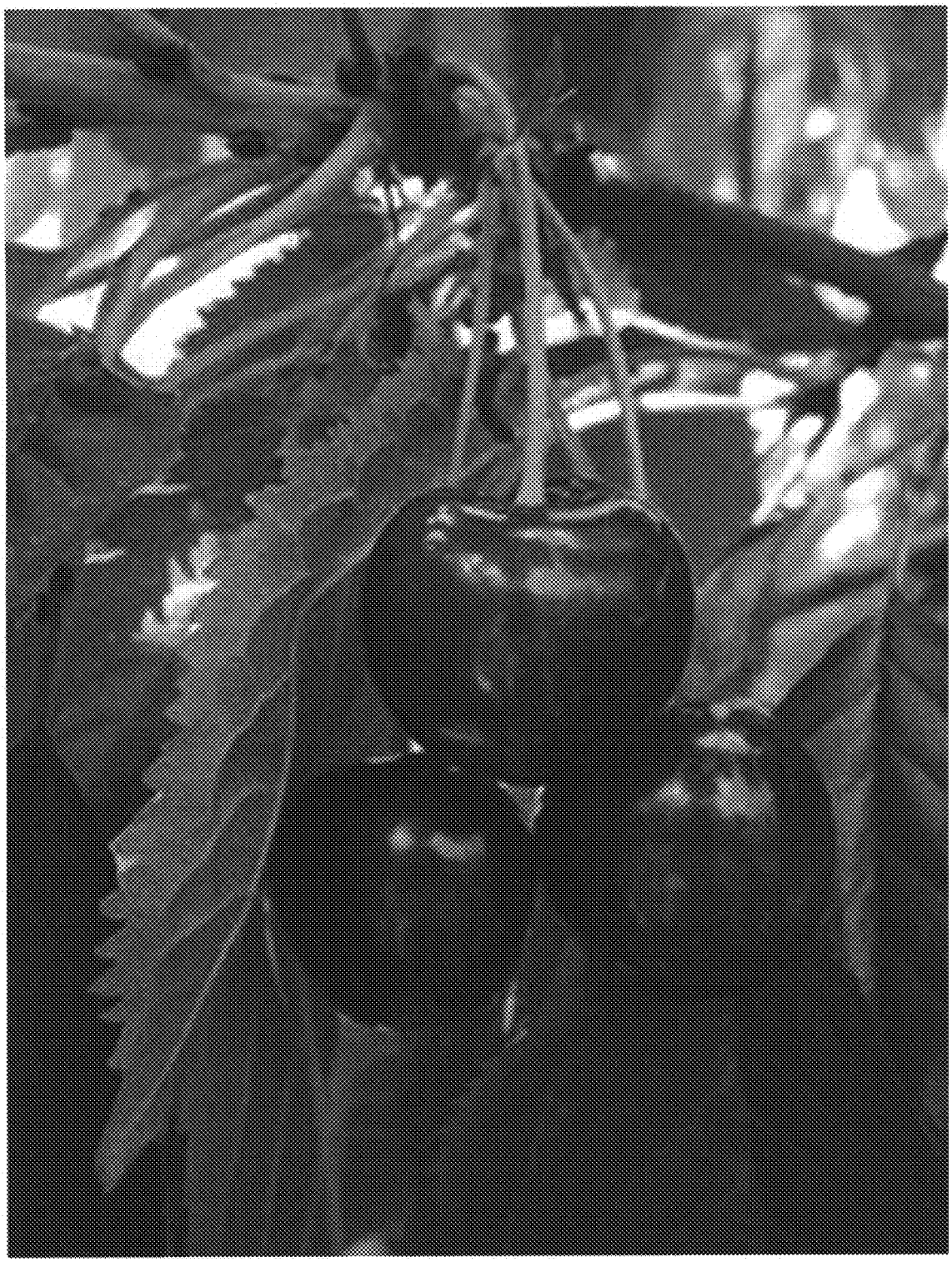
FIG. 1 is a close-up photograph of the fruit of 'HL 13822' (at approximately 11 years of age)
Figure 2:
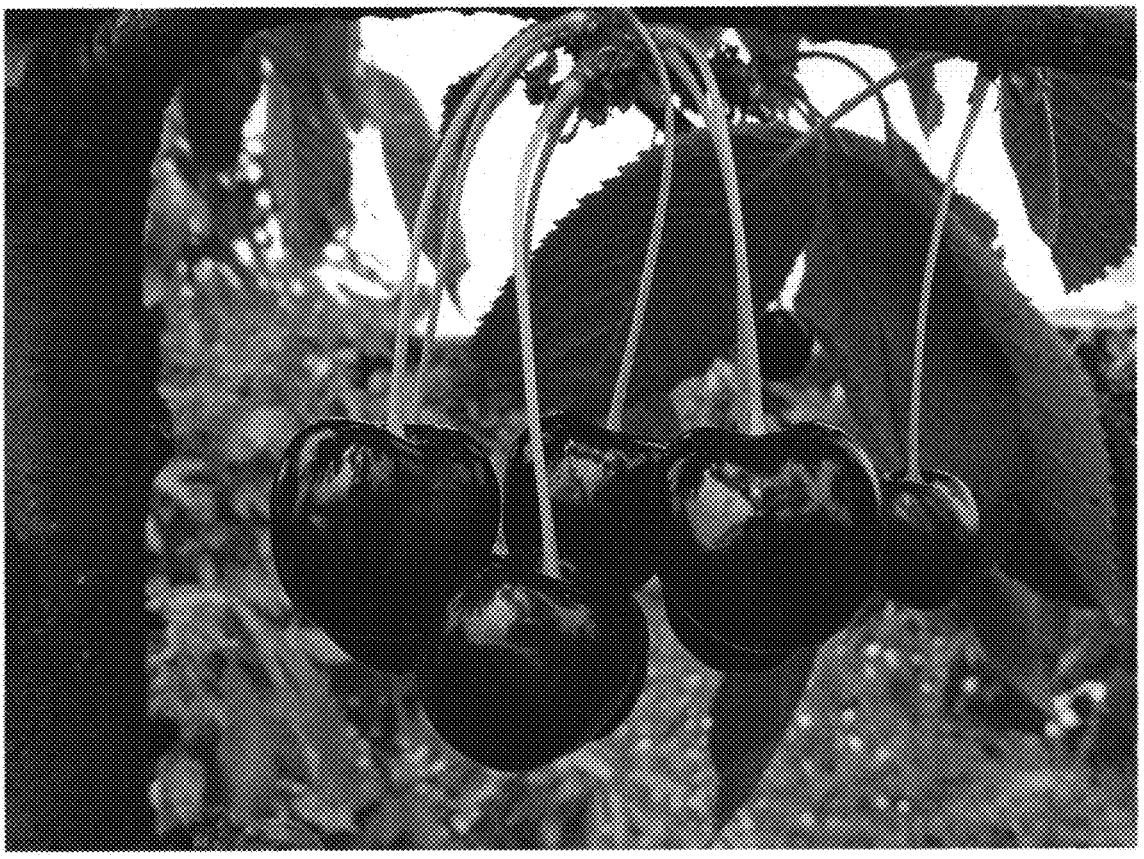
FIG. 2 is another close-up photograph of the fruit of 'HL 13822' (at approximately 11 years of age)
Figure 3:
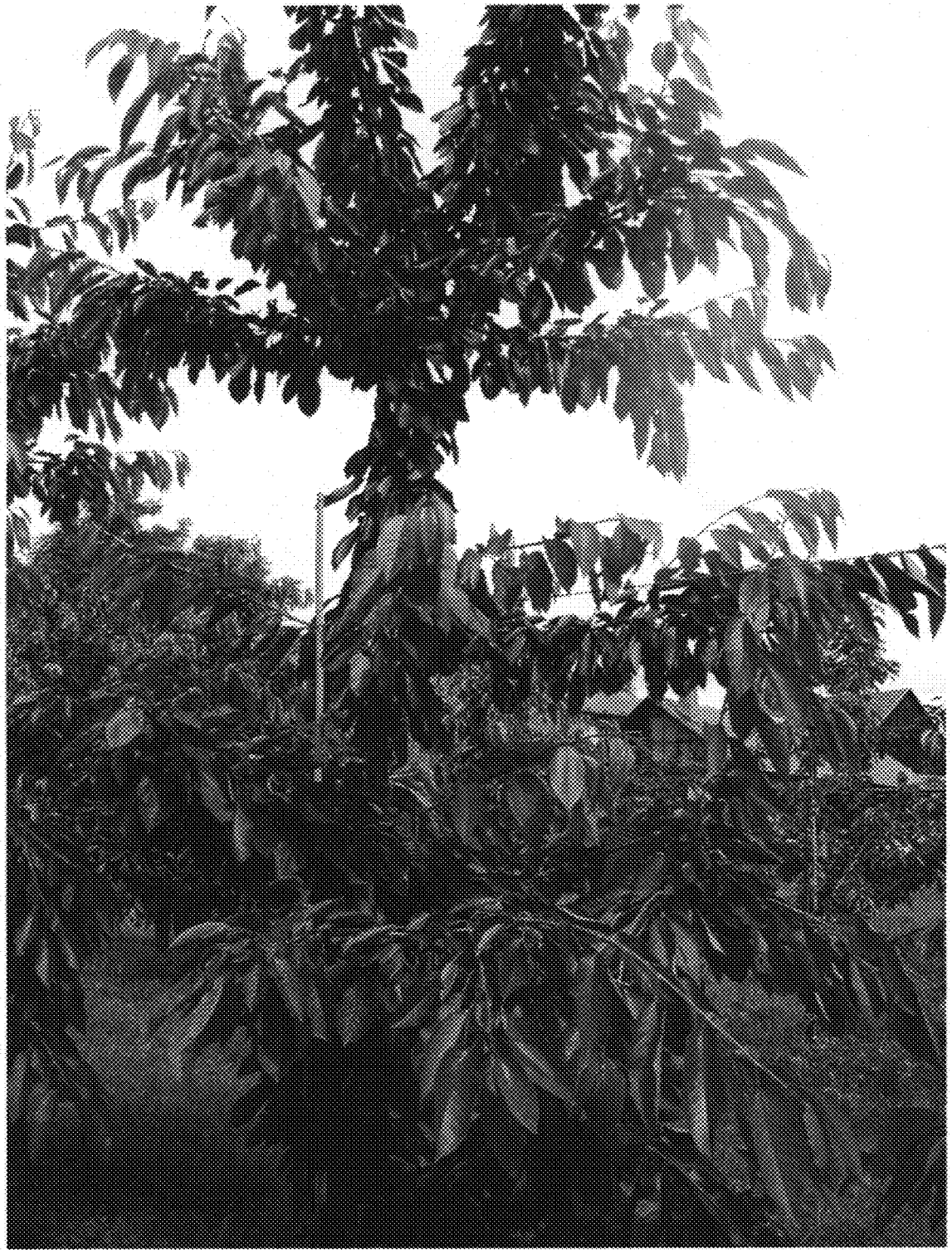
FIG. 3. is a photograph of an entire tree of the new variety (at approximately 6 years of age).

The following detailed description sets forth the characteristics of the new variety. The data which defines these characteristics were collected by asexual reproductions via grafting carried out in Holovousy, the Czech Republic. The new variety was grown outside in a non-irrigated orchard that was fertilized once per year and treated with 30 kilograms of nitrogen per hectare. The color readings were taken outside in natural daylight, and the variety was approximately 9 years old when described except where indicated otherwise. Color references are primarily to the 2007 R.H.S. Colour Chart of The Royal Horticultural Society of London, $5^{th}$ Edition.

TREE

Height: 3.0 m.
Spread: 2.5 m.
Form: Spreading
Vigor: High.
Branching: Medium to high.
Bearing: 10 kg fruit yield per plant.
Trunk:
- *Diameter.*—13.5 cm at 0.5 m above the soil line.
- *Bark color.*—191C.
- *Surface texture.*—Medium smoothness.
- *Lenticel color.*—169D.

Branches:
- *Number.*—16.
- *Diameter.*—Medium; 5.0 mm on a one-year old shoot.
- *Surface texture.*—Smooth.
- *Color.*—Generally 175C with greenish-brown coloration on the underside with silver coloration present.
- *Form.*—Slightly drooping.

*Lenticels*.—Length: 1.0 mm. Width: 1.0 mm. Shape: Globose. Density: Intermediate to high. Color: N155D.

Leaves:

*Number per branch*.—15, on a one-year old shoot that is 0.4 m long.

*Arrangement*.—Alternate.

*Length*.—Long; 21.9 mm.

*Width*.—Broad to very broad; 7.6 mm.

*Shape*.—Obovate.

*Base*.—Rounded.

*Apex*.—Mucronate.

*Margin*.—Obtusely serrate.

*Appearance*.—Upper surface: Glossy. Lower surface: Dull, with marked veining.

*Color*.—Upper surface: 143A. Lower surface: 141D.

*Petiole*.—Length: Long to very long; 6.7 mm. Diameter: 2.2 mm. Color: 150C.

*Veins*.—Type: Pinnate. Color: Upper surface: 141D. Lower surface: 144D.

Flower buds (described at BBCH stage 92):

*Number*.—4-5 per cluster.

*Length*.—7.0 mm.

*Width*.—3.0 mm.

*Color*.—N167A.

Flowers:

*Bloom timing*.—Medium to late; average time is April 21$^{st}$ in Holovousy, the Czech Republic.

*Diameter*.—Medium to large; average of 25.0 mm.

*Pollination requirements*.—Self-incompatible.

*Petals*.—Average number: 5 per flower. Arrangement: Free. Shape: Obovate. Length: 15.0 mm. Width: 14.0 mm. Apex: Rounded. Base: Mix of concave and convex. Upper and lower surface color: 155D.

*Sepals*.—Average number: 5 per flower. Length: 6.0 mm. Width: 4.0 mm. Color: 145A.

Fruit:

*Harvest*.—Average time is July 10$^{th}$ in Holovousy, the Czech Republic.

*Shape*.—Cordate.

*Size*.—Average weight: 11.4 g. Diameter: 24.8 mm. Length: 24.6 mm.

*Skin*.—Thickness: Intermediate. Tendency to crack: Limited. Color: 46A.

*Flesh*.—Aroma: Strong. Color: 45C. Texture: Intermediately fibrous and firm. Eating quality: Good; acidulate-sweet.

*Seeds*.—Number per fruit: 1. Length: 10.3 mm. Breadth: 8.8 mm. Form: Widely ellipsoidal. Color: Kernel skin: 162D. Dry stone: N155A.

*Stem*.—Length: 57.5 mm. Width: Thin to medium.

Reproductive organs:

*Stamen number*.—Average of 20.

*Filament*.—Length: 9.0 mm. Color: 155D.

*Anther*.—Shape: Cardioid. Length: 1.0 mm. Color: 163B; evolves with flowering.

*Pollen*.—Amount: Moderate to abundant. Color: 17B.

*Stigma*.—Shape: Elliptic. Color: 145A; evolves with flowering.

*Ovary color*.—142B; evolves with flowering.

Overall characteristics:

*Tree winter hardiness*.—Medium.

*Bud winter hardiness*.—Good.

*Drought tolerance*.—Good.

*Disease/pest resistance or susceptibility*.—Exhibits medium resistance to brown fruit rot (*Monilinia fructicola, M. laxa*, and *M. fructigena*) and medium susceptibility to leaf spot (*Blumeriella jaapii*).

*Shipping quality*.—Good; exhibits minimal bruising or scarring during picking, packing, and shipping.

*Storage quality*.—Good; fruit stores well for 30 days in cold storage at 1.5° C. — maintaining a nice appearance and eating quality.

*Chilling requirements*.—Approximately 1200 chilling hours total per chilling period.

I claim:

1. A new and distinct variety of cherry tree, as is herein illustrated and described.

* * * * *